US012668578B2

(12) United States Patent
Goulas et al.

(10) Patent No.: US 12,668,578 B2
(45) Date of Patent: Jun. 30, 2026

(54) FURANIC QUATERNARY AMMONIUM SALTS

(71) Applicant: Oregon State University, Corvallis, OR (US)

(72) Inventors: Konstantinos Goulas, Corvallis, OR (US); Truc Phung, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 409 days.

(21) Appl. No.: 18/472,895

(22) Filed: Sep. 22, 2023

(65) Prior Publication Data

US 2024/0010625 A1 Jan. 11, 2024

Related U.S. Application Data

(63) Continuation of application No. PCT/US2022/021426, filed on Mar. 22, 2022.

(60) Provisional application No. 63/164,938, filed on Mar. 23, 2021.

(51) Int. Cl.

| | |
|---|---|
| ***C07D 307/52*** | (2006.01) |
| ***B01J 23/44*** | (2006.01) |
| ***C07D 307/42*** | (2006.01) |
| ***C07D 307/46*** | (2006.01) |

(52) U.S. Cl.

CPC ............ *C07D 307/52* (2013.01); *B01J 23/44* (2013.01); *C07D 307/42* (2013.01); *C07D 307/46* (2013.01)

(58) Field of Classification Search

CPC ... C07D 307/52; C07D 307/42; C07D 307/46
See application file for complete search history.

(56) References Cited

FOREIGN PATENT DOCUMENTS

WO WO 2012/100342 8/2012

OTHER PUBLICATIONS

Alaupović et al., "Preparation of some trialkyl-3-(2-furyl)propylammonium iodides," *Arhiv ZA Kemiju* 27:21-23, Feb. 9, 1955 (with English machine translation).

Chen et al., "Novel rhodamine Schiff base type naked-eye fluorescent probe for sensing Fe3+ and the application in cell," *Spectrochimica Acta Part A: Molecular and Biomolecular Spectroscopy* 191:566-572, Feb. 15, 2018.

International Search Report dated Jun. 2, 2022 from International Application No. PCT/US2022/021426 (4 pages).

Ponomarev et al., "Synthesis of tertiary furan amines of the type 1-(alfa-furyl)-3-dimethylaminopropane," *Pharmaceutical Chemical Journal* 3.11:621-625, Nov. 30, 1969.

Tsvirova et al., "Comparative bactericidal activity of quaternary ammonium salts," *Pharmaceutical Chemistry Journal* 18.10:711-718, Oct. 1984.

Written Opinion dated Jun. 2, 2022 from International Application No. PCT/US2022/021426 (7 pages).

Xu et al., "Synthesis of new potential chelating agents: Catechol-bisphosphonate conjugates for metal intoxication therapy," *Heteroatom Chemistry* 15(3):251-257, Apr. 14, 2004.

*Primary Examiner* — Laura L Stockton

(74) *Attorney, Agent, or Firm* — Klarquist Sparkman, LLP

(57) ABSTRACT

Disclosed herein is a method for making a quaternary ammonium salt according to the formula

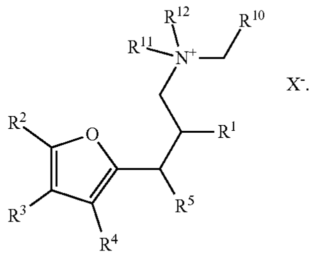

Also disclosed is a method for making the ammonium salts from an oleofuran compound. The compounds are useful as antibacterial and/or antiviral compounds and methods for administering the compounds also are disclosed.

19 Claims, No Drawings

FURANIC QUATERNARY AMMONIUM SALTS

CROSS REFERENCE TO RELATED APPLICATION

This application is a continuation of International Application No. PCT/US2022/021426, filed Mar. 22, 2022, which was published in English under PCT Article 21(2), which in turn claims the benefit of the earlier filing date of U.S. Provisional Patent Application No. 63/164,938, filed Mar. 23, 2021, both of which prior applications are incorporated herein by reference in their entireties.

FIELD

This disclosure concerns quaternary ammonium salts and a method for making the salts from oleofuran compounds.

BACKGROUND

Quaternary ammonium salts (QAS) are bactericidal compounds that disrupt bacterial cell membranes, leading to lysis. However, increased resistance to current QAS compounds exhibited by bacteria requires the discovery and production of new formulations. Additionally, the COVID-19 pandemic spurred the development of targeted virucidal formulation. Requirements for such formulations include synthetic tunability, efficacy, safety, and low cost.

SUMMARY

Disclosed herein is a method for making quaternary ammonium salts that may be useful as antibacterial and/or antiviral compounds. In some embodiments, the compound has a formula

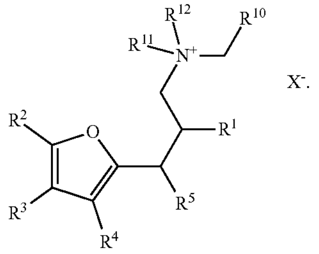

With respect to this formula, $R^1$ is H or optionally substituted $C_{1-20}$aliphatic, and may be $C_{10-10}$alkyl. And $R^{10}$ is H or optionally substituted $C_{1-20}$aliphatic, such as $C_{1-10}$alkyl. In any embodiments, $R^1$, $R^{10}$, or both, are independently optionally substituted with one or more hydroxy, amine, or carbonyl moieties, or a combination thereof.

Each of $R^2$, $R^3$, and $R^4$ independently is H, aliphatic, aldehyde, or OH, such as H or $C_{1-6}$alkyl. In some embodiments, $R^2$, $R^3$, and $R^4$ are all H. $R^5$ may be H or alkyl, such as H or $C_{1-6}$alkyl. And each of $R^{11}$ and $R^{12}$ independently is H, or aliphatic, such as H or $C_{1-6}$alkyl. In some embodiments, each of $R^{11}$ and $R^{12}$ independently is H or $C_{1-4}$alkyl, and may be methyl.

In any embodiments, X is halide or OH, such as Cl, Br, I, F, or OH, and may be Cl, Br, I or OH. In some embodiments, X is Cl or Br, and in certain embodiments, X is Cl.

In a particular embodiment, $R^1$ is $C_6$alkyl; $R^{10}$ is $C_3$alkyl; $R^2$, $R^3$, and $R^4$ are all H; $R^{11}$ and $R^{12}$ are both methyl; and X is Cl.

Also disclosed herein are embodiments of a pharmaceutical composition comprising one or more of the disclosed compounds and a pharmaceutically acceptable excipient.

A method for making the quaternary ammonium salts also is disclosed herein. In some embodiments, the method comprises forming a mixture comprising a compound having a formula

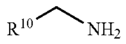

and a compound having a formula A-1

A-1

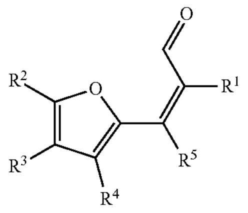

to form a compound having a formula A-2

A-2

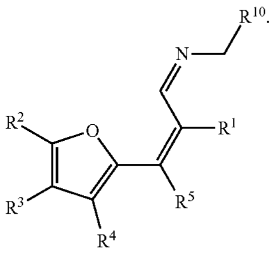

The method may further comprise exposing the compound of formula A-2 to reducing conditions, such as a reducing agent or hydrogen gas in the presence of a catalyst, to form a compound having a formula A-3

A-3

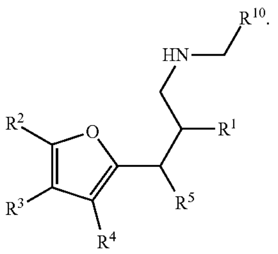

And the method may also comprise treating the compound of formula A-3 with a compound of formula $R^{11}X$ and a compound of formula $R^{12}X$ to form a compound having a formula A-4

A-4

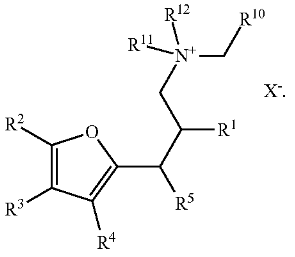

With respect to the formulas A-1 to A-4, $R^1$, $R^2$, $R^3$, $R^4$, $R^5$, $R^{10}$, $R^{11}$ and $R^{12}$ are as defined herein; and each X independently is halide or OH. In some embodiments, the X moieties in $R^{11}X$ and $R^{12}X$ are the same, but in other embodiments they are different. In some embodiments, $R^{11}$ and $R^{12}$ are the same, but in other embodiments they are different. In some embodiments, the compound of formula $R^{11}X$ and the compound of formula $R^{12}X$ are the same, but in other embodiments, they are different.

In some embodiments, the reducing agent is a borohydride reagent, such as sodium borohydride. In other embodiments, the reducing conditions comprise hydrogen as in the presence of a catalyst, such as a palladium catalyst.

And/or in particular embodiments, each X is Cl or Br, typically Cl.

Further disclosed is a method for using the compounds. In some embodiments the method comprises administering to a subject in need thereof, a compound or composition thereof as disclosed herein.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

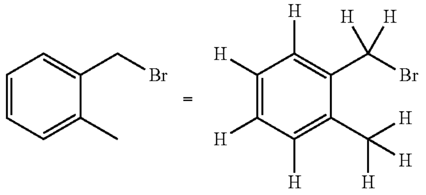

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms.

"Aldehyde" refers to the moiety —CHO, which also may be shown as —C(=O)H.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$), from one to six ($C_{1-6}$), from one to four carbon atoms ($C_{1-4}$) or two to twenty two ($C_{2-22}$) or 6 to 18 ($C_{6-18}$) for a saturated acyclic aliphatic group or moiety, from two to twenty-five carbon atoms ($C_{2-25}$); for example, from two to fifteen ($C_{2-15}$), from two to ten ($C_{2-10}$), from two to six ($C_{2-6}$), or from two to four carbon atoms ($C_{2-4}$) for an unsaturated acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Substituents on an aliphatic group or moiety may be any substituents understood by a person of ordinary skill in the art to be compatible with the synthesis of the oleofuran compounds. Exemplary substituents include, but are not limited to, hydroxyl, amine, carbonyl (C═O), aldehyde, or aliphatic, such as alkyl, alkenyl, alkynyl, and straight chain, cyclic and branched versions thereof.

"Alkyl" refers to a saturated aliphatic hydrocarbyl group having from 1 to 25 ($C_{1-25}$) or more carbon atoms, such as from 1 to 10 ($C_{1-10}$) carbon atoms, from 1 to 6 ($C_{1-6}$) carbon atoms, or from 2 to 22 ($C_{2-22}$) carbon atoms or from 6 to 18 ($C_{6-18}$) carbon atoms. An alkyl moiety may be substituted or unsubstituted. This term includes, by way of example, linear and branched hydrocarbyl groups such as methyl ($CH_3$), ethyl ($—CH_2CH_3$), n-propyl ($—CH_2CH_2CH_3$), isopropyl ($—CH(CH_3)_2$), n-butyl ($—CH_2CH_2CH_2CH_3$), isobutyl ($—CH_2CH_2(CH_3)_2$), sec-butyl ($—CH(CH_3)(CH_2CH_3)$), t-butyl ($—C(CH_3)_3$), n-pentyl ($—CH_2CH_2CH_2CH_2CH_3$), neopentyl ($—CH_2C(CH_3)_3$), hexyl ($C_6H_{13}$), heptyl ($C_7H_{15}$), octyl ($C_8H_{17}$), decyl ($C_{10}H_{21}$), dodecyl ($C_{12}H_{25}$), tetradecyl ($C_{14}H_{29}$), hexadecyl ($C_{16}H_{33}$), octadecyl ($C_{18}H_{37}$) or eicosanyl ($C_{20}H_{41}$). "Amine" refers to a —N(R)R' moiety where R and R' are independently H, aliphatic, such as alkyl, alkenyl or alkynyl, or R and R' together with the nitrogen to which they are attached for a 5- to 7-membered heterocyclic ring, optionally containing one, two or three further heteroatoms selected from O, N or S, and/or optionally substituted with one, two or three aliphatic groups, such as alkyl groups.

"Fatty alcohol" refers to an aliphatic alcohol compound having at least 4 carbon atoms in the aliphatic chain, such as from 4 to 30 carbon atoms or more, such as from 4 to 30, from 4 to 24, from 4 to 20, or from 8 to 20. Unless otherwise specified, the carbon chain in a fatty alcohol may be a straight chain, or it may be branched, cyclic, or a combination thereof.

"Hydroxyl" and "hydroxy" refer to a —OH moiety.

As used herein, the term "$C_{1-25}$ alcohol" and the like, refers to an alcohol, typically an aliphatic alcohol that comprises from 1 to 25 carbon atoms in addition to at least one OH moiety.

As used herein, a "hydrogen donor" is a compound that donates one or more hydrogens to another compound during a chemical reaction. For example, an alcohol may be a hydrogen donor if hydrogen is transferred from the alcohol to another compound during a chemical reaction and the alcohol forms a carbonyl moiety in place of the hydroxyl.

"Pharmaceutically acceptable excipient" refers to a substantially physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, as a carrier, flavoring, thickener, diluent, buffer, preservative, or surface active agent and/or to modify properties of a pharmaceutical composition. Examples of excipients include, but are not limited, to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

II. Quaternary Ammonium Salts

Disclosed herein are quaternary ammonium salts having a formula

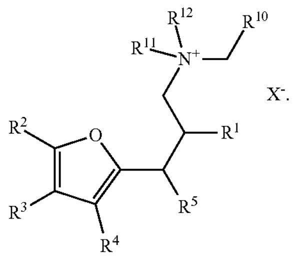

With respect to this formula, $R^1$ is H or optionally substituted $C_{1-20}$aliphatic, such as alkyl, alkenyl or alkynyl. $R^1$ may be $C_{1-10}$aliphatic, such as $C_{1-10}$alkyl, $C_{2-10}$alkyl, $C_{4-8}$alkyl, and may be $C_6$ alkyl. $R^1$ may be a straight chain, or branched chain, and/or may be cyclic or comprise cyclic moieties. In some embodiments, $R^1$ is unsubstituted, but in other embodiments, $R^1$ is substituted, such as with one or more hydroxyl, amine, and/or carbonyl moieties.

Each of $R^2$, $R^3$, and $R^4$ independently is H, aliphatic, aldehyde, or OH, such as H, alkyl, alkenyl, aldehyde, or OH, and typically H or alkyl, such as H or $C_{1-6}$alkyl. In some embodiments, at least $R^2$ and may be all of $R^2$, $R^3$ and $R^4$ are H.

$R^5$ is H or alkyl, such as H or $C_{1-3}$alkyl, and in some embodiments, $R^5$ is H.

$R^{10}$ is H or optionally substituted $C_{1-20}$aliphatic, such as alkyl, alkenyl or alkynyl. $R^{10}$ may be $C_{1-10}$aliphatic, such as $C_{1-10}$alkyl, $C_{2-10}$alkyl, $C_{1-6}$alkyl, and may be $C_3$ alkyl. $R^{10}$ may be a straight chain, or branched chain, and/or may be cyclic or comprise cyclic moieties. In some embodiments, $R^{10}$ is unsubstituted, but in other embodiments, $R^{10}$ is substituted, such as with one or more hydroxyl, amine, and/or carbonyl moieties.

Each of $R^{11}$ and $R^{12}$ independently is H, or aliphatic, such as alkyl, and may be $C_{1-6}$ alkyl, such as $C_{1-4}$alkyl, and may be methyl, ethyl, propyl or isopropyl, such as methyl.

And each X independently is a suitable leaving group and/or counter ion, such as a halide (such as Cl, Br, I, or F, preferably Cl, Br, or I, and may be Cl or Br), or hydroxy. And in certain embodiments, X is Cl.

In a particular embodiment, $R^1$ is $C_6$alkyl, $R^{10}$ is $C_3$alkyl, each of $R^2$, $R^3$ and $R^4$ is H, each of $R^{11}$ and $R^{12}$ is methyl, and X is Cl.

III. Method for Making Quaternary Ammonium Salts

Also disclosed herein is a method for making the quaternary ammonium salts. The method may comprise reductive amination from an oleofuran precursor, such as an oleofuran compound described below.

A. Method for Making Oleofuran Precursor

Disclosed herein is a method for making oleofuran compounds from an alcohol, such as a fatty alcohol, and a furan carbonyl compound, such as a furan aldehyde or ketone. Oleofuran compounds made by the disclosed method are useful as precursors for making oleofuran sulfonate compounds, such as oleofuran sulfonate detergents. The disclosed method may comprise two steps that may be performed in a single pot or in separate reactors. A person of ordinary skill in the art understands that if the reaction is performed in a single pot, the second catalyst may be added part way through the reaction, so that the aldehyde or ketone is not reduced by the catalyst too early in the reaction progression.

In some embodiments, the method comprises forming a first mixture comprising an alcohol, such as a fatty alcohol, and a compound according to formula 1 in the presence of a first catalyst Formula 1

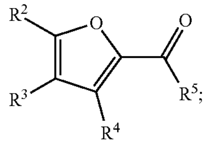

heating the first mixture at a first temperature of from 100° C. to 200° C. to form a compound according to formula 2

Formula 2

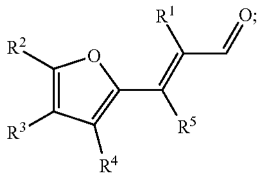

and heating the compound according to formula 2 at a second temperature of from 120° C. to 220° C. in the presence of hydrogen and a second catalyst to form one or more compounds according to formula 3

Formula 3

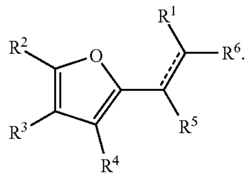

With respect to Formulas 1, 2 and 3, $R^1$ is aliphatic, typically alkyl, such as $C_{2-22}$alkyl or $C_{6-18}$alkyl. Each of $R^2$, $R^3$, and $R^4$ independently is H, aliphatic, aldehyde, or OH, such as H, alkenyl, aldehyde, or OH, typically H or alkyl, such as H or $C_{1-6}$alkyl, and in some embodiments, at least $R^2$ and may be $R^2$, $R^3$ and $R^4$ are H. $R^5$ is H or alkyl, such as H or $C_{1-3}$alkyl, and in some embodiments, $R^5$ is H. $R^6$ is H, $CH_3$, or $CH_2OH$. And --- indicates that a bond may be a single bond or a double bond. And in some embodiments, the fatty alcohol has a formula

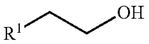

where $R^1$ is as defined herein for Formulas 1-3.

The first catalyst may be a basic catalyst and/or may comprise magnesium, such as magnesium oxide. In some embodiments, the first catalyst comprises a mixed oxide of magnesium and aluminum. In other embodiments, the first catalyst is or comprises a nickel catalyst. The nickel catalyst may be a Ni(II) catalyst, such as a homogeneous Ni(II) catalyst, for example, nickel (II) acetylacetonate, anhydrous $NiCl_2$, hydrous $NiCl_2$, or phosphine-ligated $Ni^{2+}$ catalysts, such as bis(triphenylphosphine)nickel(II) dichloride or bis(tricyclohexylphosphine)nickel(II) dichloride.

In some embodiments of the method, forming the first mixture comprises forming the first mixture in the presence of a base. The base may be an organic base, inorganic base, or a combination thereof. In certain embodiments, the base is an organic base such as pyrrolidine, or a trialkylamine, for example triethylamine or trimethylamine.

Heating the compound according to formula 2 in the presence of hydrogen may comprise heating the compound in the presence of hydrogen gas. However, in other embodiments, the compound is heated in the presence of a hydrogen donor. The hydrogen donor may be an alcohol, such as a secondary alcohol. A hydrogen donor alcohol may have a formula

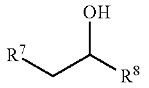

where each of $R^7$ and $R^8$ independently is H or alkyl. $R^7$ and $R^8$, together with the carbon atoms to which they are attached, may form a $C_{2-25}$ carbon chain. And in particular embodiments, $R^8$ is $CH_3$ and $R^7$ is H or $C_{1-18}$ alkyl, such as H or $C_{1-8}$ alkyl. Exemplary alcohols useful as hydrogen donors in the disclosed method include, but are not limited to, 2-propanol, 2-butanol, 2-pentanol, 2-hexanol, 2-heptanol or a combination thereof.

The second catalyst may be a metal oxide, a metallic catalyst, or a combination thereof. In some embodiments, the metal oxide comprises an oxide of Cu, Pd, Ru, Ir, Ti, Sn, Mo, Fe, In, W, Ni, Co, Zn, V or a combination thereof and/or the metallic catalyst comprises Re, Ni, Cu, Pd, Ru, Rh, Pt, Ag, Au, Ir, Zn or mixtures thereof. The metallic catalyst may further comprise a support substrate, such as carbon or a metal oxide, which may be the same metal oxide as is in the second catalyst, or a different metal oxide. In some embodiments, the second catalyst comprises the metallic catalyst supported on the metal oxide. In some embodiments, a portion of the metal oxide may be a film on top of a metallic substrate. In certain embodiments, the second catalyst is, or comprises, Ru/C, $RuO_2 \cdot H_2O$, $In_2O_3$, or a combination thereof.

In a particular embodiment, the method comprises forming a first mixture comprising an alcohol having a formula

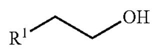

and a compound according to formula 1 in the presence of a first catalyst comprising magnesium and aluminum oxides Formula 1

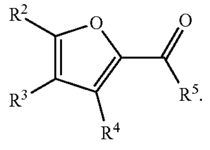

The first mixture is then heated at a first temperature of from 130° C. to 170° C. to form a compound according to formula 2

Formula 2

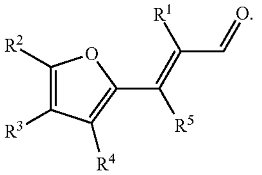

The compound according to formula 2 is then heated at a second temperature of from 150° C. to 200° C. in the presence of a secondary alcohol having a formula

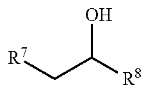

and a second catalyst comprising a metallic catalyst and a metal oxide to form one or more compounds according to formula 3

Formula 3

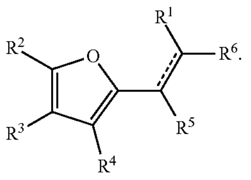

In some embodiments, $R^1$, $R^2$, $R^3$, $R^4$, $R^5$, $R^6$, $R^7$ and $R^8$ are as previously defined. And in certain embodiments, $R^1$ is $C_{2-22}$alkyl; each of $R^2$, $R^3$, and $R^4$ independently is H or $C_{1-6}$alkyl; $R^5$ is H; $R^6$ is H, $CH_3$, or $CH_2OH$; $R^7$ is H or $C_{1-18}$ alkyl; and $R^8$ is $CH_3$.

And in any embodiments, the one or more compounds according to formula 3 may be selected from

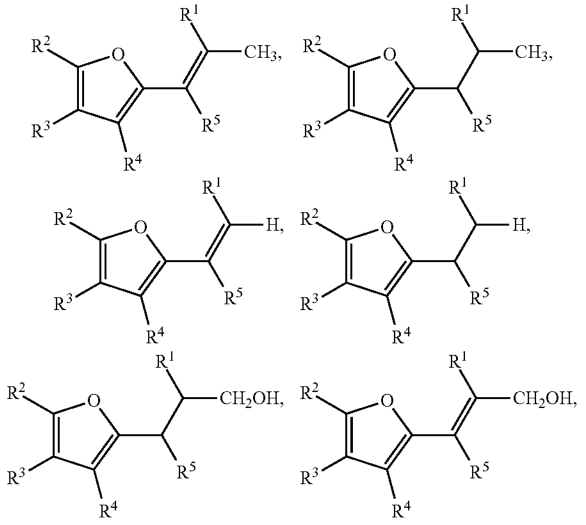

or a combination thereof.

I. Step 1

The first step of the process is a tandem dehydrogenation and aldol condensation reaction, as shown in Scheme 1.

Scheme 1

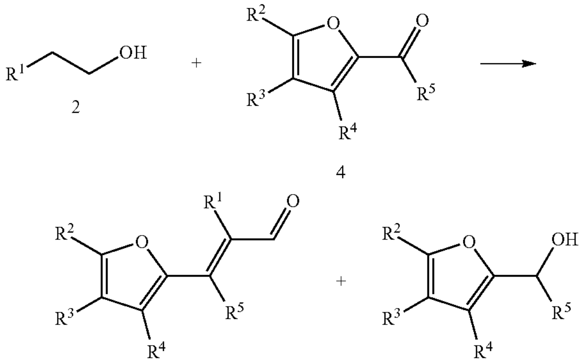

2 4 6 8

With respect to Scheme 1, compound 2 is a fatty alcohol where $R^1$ is aliphatic, such as alkyl, alkenyl, or alkynyl, typically alkyl, such as $C_{2-22}$alkyl or $C_{6-18}$alkyl. Each of $R^2$, $R^3$, and $R^4$ independently is H, aliphatic, aldehyde, or OH, such as H, alkyl, alkenyl, aldehyde, or OH, and in certain embodiments, each of $R^2$, $R^3$, and $R^4$ independently is H or alkyl, such as H or $C_{1-6}$alkyl. In some embodiments, $R^2$ is H, and in certain embodiments, two of $R^2$, $R^3$ and $R^4$ is H, or $R^2$, $R^3$, and $R^4$ are all H. And $R^5$ is H or alkyl, such as H or $C_{1-6}$alkyl, or H or $C_{1-3}$alkyl, typically H or methyl, and in some embodiments, $R^5$ is H. In a particular embodiment, $R^2$, $R^3$, $R^4$ and $R^5$ are all H. Additionally, a person of ordinary skill in the art understands that there are various possible stereoisomers of compound 6 that are contemplated by the disclosure. For example, Scheme 1 shows the cis isomer of compound 6 with respect to $R^1$ and the furan ring about the double bond as an example structure. However, compound 6 also may exist as the trans isomer with respect to the furan ring and $R^1$, or compound 6 may comprise a mixture of cis and trans isomers, and both options are contemplated.

The reaction proceeds with a stoichiometric ratio of 2:1 aldehyde or ketone to fatty alcohol. That is, in the reaction, 2 equivalents of aldehyde or ketone are used per 1 equivalent of fatty alcohol, and one equivalent of aldehyde or ketone is converted to alcohol 8 during the reaction (Scheme 1). Accordingly, in some embodiments, aldehyde or ketone 4 and fatty alcohol 2 are in a molar ratio of 2:1. However, in other embodiments, the molar ratio of aldehyde or ketone 4 to fatty alcohol 2 is from 0.5:1 (i.e., excess alcohol) to 5:1 (i.e., excess furan compound) is used in the reaction.

The reaction may be performed in the presence of a catalyst. Suitable catalysts include any catalyst that facilitates the reaction in step 1. In some embodiments, the catalyst is a basic catalyst, such as a metal oxide catalyst, for example a magnesium oxide catalyst, or the catalyst may be a mixed metal oxide catalyst, for example, comprising both Mg and Al, such as hydrotalcite-derived mixed oxide comprising an Mg:Al ratio of 3:1, or $TiO_2$, $CeO_2$, $ZrO_2$, CaO, BaO, SrO, $Al_2O_3$, $SiO_2$, hydrotalcites, hydroxyapatites, amine-functionalized silica or any combination thereof.

In other embodiments, the catalyst may be a nickel catalyst, such as a Ni(II) catalyst. The nickel catalyst may be a homogeneous Ni catalyst, such as a homogeneous Ni(II) catalyst, for example, nickel (II) acetylacetonate, anhydrous $NiCl_2$, hydrous $NiCl_2$, or phosphine-ligated $Ni^{2+}$ catalysts. The Ni catalyst may be use in combination with a base, such as an organic base, inorganic base, or a combination thereof. Suitable bases include, but are not limited to, an amine, such as triethylamine, pyrrolidine or diisopropylethylamine; a carbonate, such as potassium carbonate or sodium carbonate, heterogeneous bases, such as amine-functionalized silica or any of the oxides mentioned in the previous paragraph; or a combination thereof.

In any embodiments, the reaction may be performed in a solvent suitable to facilitate the reaction, such as a aprotic solvent, for example, but without limitation, toluene, xylene, or an alkane, including branched and cycloalkanes, such as cyclohexane, cycloheptane, cyclooctane, n-heptane, n-octane, or a combination thereof. In embodiments where the reaction proceeds in the presence of an organic base, such as a trialkylamine, the organic base also may be used as the solvent. For example, triethylamine or diisopropylethylamine may be used as both the base and a solvent, or just as a base or just as a solvent. Additionally, or alternatively, the reaction may be performed in an excess of the fatty alcohol such that the excess fatty alcohol acts as a reaction solvent.

The reaction proceeds at a temperature suitable to facilitate compound 6 formation. In some embodiments, the reaction is performed at a temperature of from 100° C. or less to 200° C. or more, such as from 100° C. to 200° C., or from 130° C. to 170° C. Additionally, or alternatively, the reaction may proceed at a suitable pressure, such as an ambient pressure or an autogenous pressure where the reaction proceeds in a sealed reaction vessel and the pressure increases inside the vessel as the reaction temperature increases. The reaction may be heated for from greater than zero to 48 hours or more, such as from 1 hour to 48 hours, from 6 hours to 42 hours, from 12 hours to 36 hours, or from 18 hours to 24 hours.

After heating, the reaction mixture may be used without purification, or the catalyst may be removed by any suitable technique, such as filtration or decanting. The resulting liquid phase may be used without further purification, or compound 6 may be partially or fully isolated from the liquid phase. In some embodiments, the liquid phase is treated to increase the concentration of compound 6 in the liquid phase, such as by distilling off at least a portion of the solvent, unreacted starting materials, and/or unwanted reaction products such as compound 8.

II. Step 2

The second step of the synthesis is a hydrodeoxygenation reaction as shown in Scheme 2.

Scheme 2

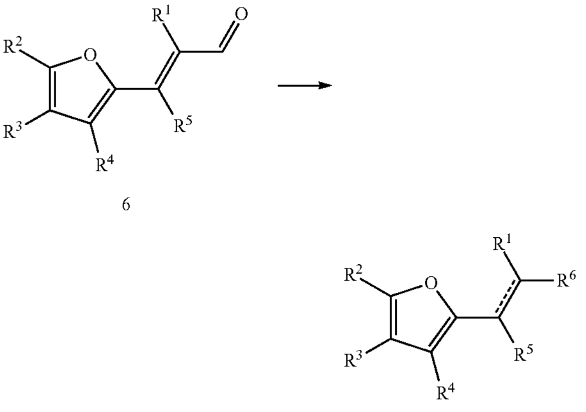

6

10

With respect to Scheme 2, $R^1$-$R^5$ are as defined in Scheme 1, $R^6$ is H, $CH_3$ or $CH_2OH$, and '---' indicates that the bond may be either a single or a double bond. Accordingly, compound 10 may be a single compound or a mixture of compounds, such as a mixture of 2, 3, 4, 5, or 6 compounds shown by formulas 10-a, 10-b, 10-c, 10-d, 10-e, and 10-f below:

10-a

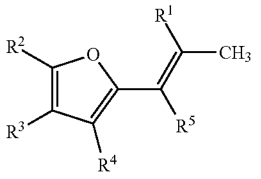

10-b

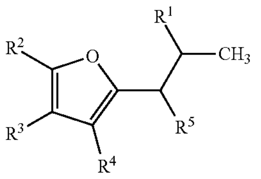

10-c

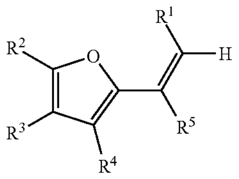

-continued 10-d

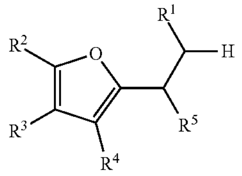

10-e

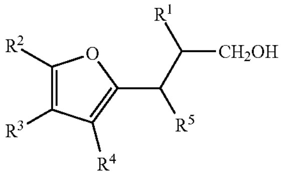

10-f

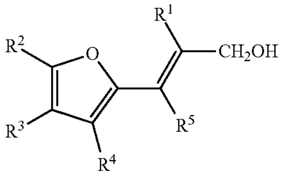

If the double bond is present, compound 10 may be the cis isomer, the trans isomer or a mixture of the cis and trans isomers with respect to the orientation of the furan and $R^1$ about the double bond. That is, compounds 10-a, 10-c and 10-f may be cis, trans, or a mixture thereof with respect to the furan and $R^1$.

The reaction may proceed in the presence of hydrogen and/or in the presence of a hydrogen donor. The hydrogen donor may be any suitable hydrogen donor, such as an alcohol, typically a $C_{1-25}$ or $C_{3-21}$ alcohol, and may be a primary or secondary alcohol. Additionally, mixture of alcohols may be used, such as 2, 3, 4 or more alcohols. In some embodiments, a secondary alcohol is used, such as a $C_{3-21}$ secondary alcohol or $C_{3-11}$ secondary alcohol. During the reaction, the alcohol moiety may be converted to a carbonyl moiety. One such exemplary embodiment is shown in Scheme 3.

Scheme 3

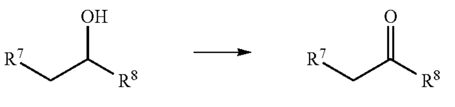

12 14

With respect to Scheme 3, each of $R^7$ and $R^8$ independently is H or alkyl such that $R^7$ and $R^8$, together with the carbon atoms to which they are attached, forms a $C_{2-25}$ carbon chain. In some embodiments, alcohol 12 is a primary alcohol where $R^8$ is H, but in other embodiments, alcohol 12 is a secondary alcohol and $R^8$ is not H. In certain embodiments, $R^7$ and $R^8$, together with the carbon atoms to which they are attached, forms a $C_{3-21}$ secondary alcohol, such as a $C_{3-11}$ secondary alcohol, and in particular embodiments, $R^8$ is $CH_3$ and $R^7$ is H or $C_{1-18}$ alkyl, such as $C_{1-8}$ alkyl. Exemplary alcohols that are useful in the reaction include, but are not limited to, 2-propanol, 2-butanol, 2-pentanol, 2-hexanol, 2-heptanol or any mixture thereof. And in some embodiments of scheme 2, an excess of alcohol 12 is used, such as a molar ratio of alcohol to compound 6 of from 10:1 to 1000:1.

Additionally, the reaction may proceed in the presence of a catalyst. The catalyst may be a single catalyst or it may be a mixture of catalysts. The catalyst may comprise a metallic catalyst, a metal oxide, or a mixture thereof. The metal oxide may comprise a single metal, or multiple metals, such as 2, 3, 4, or more metals, in addition to oxygen. And the metallic catalyst may comprise a single metal or a mixture of metals, such as 2, 3, 4, or more metals. Typically, the metallic catalyst is provided on a support substrate. Suitable support substrates include any substrate that facilitates the metallic catalyst functioning as a catalyst in the reaction. In some embodiments, the support substrate is carbon, but in other embodiments, the support substrate is, or comprises, a metal oxide. The metal oxide may be the same metal oxide that is included in the catalyst, or it may be a different metal oxide, such as a non-catalytic metal oxide. Metals suitable for use as in the metallic catalyst include, but are not limited to, Re, Ni, Cu, Pd, Ru, Rh, Pt, Ag, Au, Jr, Zn or mixtures thereof. Elements suitable for use as oxides include but are not limited to Cu, Pd, Ru, Jr, Ti, Sn, Mo, Fe, In, W, Ni, Co, Zn, V. In some embodiments comprising both a metallic catalyst and a metal oxide, the metal(s) in the metallic catalyst and the metal oxide may be the same, or they may be different. In certain disclosed embodiments, the catalyst is, or comprises, Ru/C, $RuO_2 \cdot H_2O$, $In_2O_3$, or a combination thereof.

Suitable temperatures for the reaction include any temperature that facilitates the formation of the desired products. In some embodiments, the reaction is heated at a temperature of 120° C. or less to 240° C. or more, such as 120° C. to 220° C., of from 150° C. to 220° C., or from 150° C. to 200° C. Additionally, or alternatively, the reaction may proceed at a suitable pressure, such as an ambient pressure or an autogenous pressure where the reaction proceeds in a sealed reaction vessel and the pressure increases inside the vessel as the reaction temperature increases. The reaction may be heated for from greater than zero to 48 hours or more, such as from 1 hour to 48 hours, from 4 hours to 42 hours, from 4 hours to 36 hours, or from 6 hours to 24 hours.

In some embodiments, the reaction temperature, pressure, reaction time and/or catalyst may be selected to facilitate formation of desired compounds according to one or more, such as 1, 2, 3, 4, 5 or 6, of formulas 10-a, 10-b, 10-c, 10-d, 10-e and/or 10-f.

After heating, the oleofuran product(s) may be isolated by techniques known to persons of ordinary skill in the art. For example, the catalyst may be removed by any suitable technique, such as filtration or decanting, and the resulting liquid may be heated to distill of at least a portion, or substantially all, of the solvent, unreacted starting materials such as excess alcohol, and/or unwanted reaction products such as compound 14. Typically, for detergent production, compound is left as a mixture of oleofuran compounds that is not further purified.

B. Method for Making the Quaternary Ammonium Salts

The disclosed quaternary ammonium salts may be made from an oleofuran precursor, such as a compound according to Formula 3 above. In some embodiments, the disclosed quaternary ammonium salts are made according to Scheme 4, while in other embodiments, the ammonium salts are made according to Scheme 5.

Scheme 4

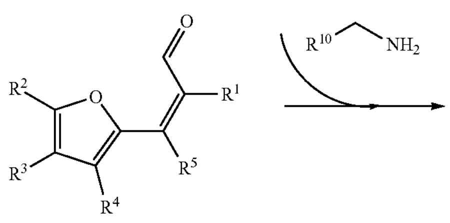

6

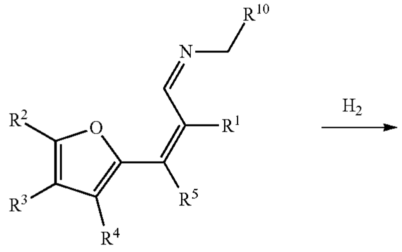

52

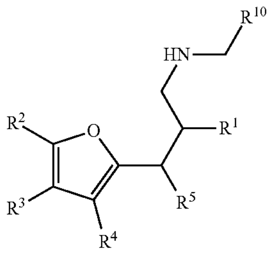

53

53 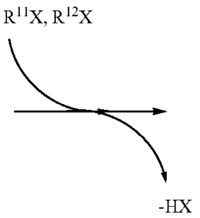

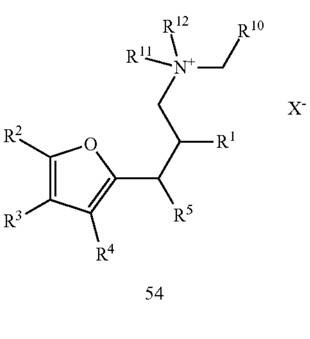

54

Scheme 5

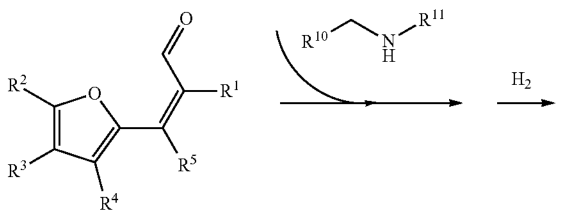

6

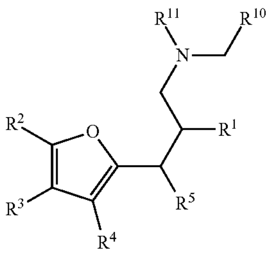

53′

53′ 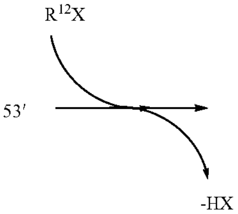

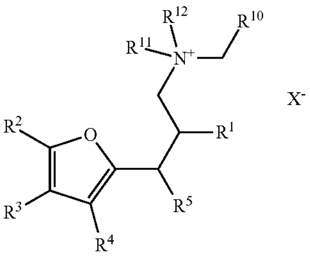

54

With respect to Schemes 4 and 5, $R^1$-$R^5$ are as defined above for Schemes 1-3. In some embodiments, each of $R^1$ and $R^{10}$ independently is H or $C_1$-$C_{20}$ aliphatic, such as alkyl, alkenyl or alkynyl, and may be a straight chain, branched, or cyclic, and/or may include cyclic moieties. In some embodiments, $R^1$ and/or $R^{10}$ is unsubstituted, but in other embodiments, one or both of $R^1$ and $R^{10}$ is substituted, such as with one or more hydroxyl, amine, and/or carbonyl moieties. In certain embodiments, $R^1$ is $C_{2-10}$alkyl, and may be $C_6$ alkyl. And/or in certain embodiments, $R^{10}$ is $C_{1-6}$alkyl, such as $C_{2-4}$alkyl, and may be $C_3$alkyl.

Each of $R^{11}$ and $R^{12}$ independently is H, or aliphatic, such as alkyl, and may be $C_{1-6}$alkyl, such as $C_{1-4}$alkyl, and may be methyl, ethyl, propyl or isopropyl, such as methyl.

And each X independently is a suitable leaving group and/or counter ion, such as a halide (such as Cl, Br, I, F, preferably Cl, Br or I, and may be Cl or Br), tosylate, mesylate, or hydroxy. And in certain embodiments, X is Cl.

Also with respect to Schemes 4 and 5, compound 6 is treated with the amine compound to form compound 52 or simultaneously with an amine and a reducing agent, including molecular hydrogen, or a solid reducing agent, such as a borohydride, for example sodium borohydride, sodium triacetoxyborohydride, or sodium cyanoborohydride, optionally in the presence of a suitable catalyst, for example a palladium catalyst, with or without appropriate promoters such as $Pd/SiO_2$ or Pd/C. The reaction may proceed in a suitable solvent, such as an aprotic solvent, for example, toluene, xylene, acetonitrile, THF, DMF, or a combination thereof, or it may proceed in a protic solvent, such as an alcohol, for example methanol, ethanol, isopropanol, or a combination thereof. The method may proceed with the removal of water, such as by azeotropic removal and/or a suitable drying agent, such as molecular sieve.

Compound 52 is reduced to compound 53 by a suitable method, such as hydrogenation, optionally in the presence of a suitable catalyst, for example a palladium catalyst, with or without appropriate promoters such as $Pd/SiO_2$ or Pd/C; or with a reducing agent, such as a borohydride, for example sodium borohydride, sodium triacetoxyborohydride, or sodium cyanoborohydride. The reaction may proceed in a suitable method, such as an alcohol, for example methanol, ethanol or isopropanol; an aprotic solvent, such as toluene, or THF; or any combination thereof. In some embodiments, compound 52 is isolated and may be purified before the reduction, but in other embodiments, compound 52 is treated in situ to form compound 53.

Compounds 53 or 53' are then treated with compounds $R^{11}X$ and/or $R^{12}X$ to form compound 54. Compounds $R^{11}X$ and $R^{12}X$ may be the same or they may be different. And the respective X groups may be the same or they may be different. The reaction proceeds in a suitable solvent, such as an aprotic solvent, for example THF, acetone, toluene, cyclohexane, or a combination thereof. Optionally, the reaction may be performed in the presence of a suitable additive, such as butylated hydroxytoluene.

IV. Method for Using the Quaternary Ammonium Salts

The disclosed compound are useful as antibacterial and antiviral compounds. Certain embodiments are useful against gram+ bacteria (for example, Enterococci), gram− bacteria (for example, *E. coli*), viruses (for example, SARS-COV-2), or a combination thereof.

I. Compositions

Pharmaceutical compositions for administration to a subject, such as a human or animal subject, can include at least one further pharmaceutically acceptable additive such as carriers, thickeners, diluents, buffers, preservatives, surface active agents and the like, in addition to the disclosed compound(s). Pharmaceutical compositions can also include one or more additional active ingredients such as antimicrobial agents, anti-inflammatory agents, anticancer agents, anesthetics, and the like. The pharmaceutically acceptable carriers useful for these formulations are conventional. *Remington's Pharmaceutical Sciences*, by E. W. Martin, Mack Publishing Co., Easton, PA, 19th Edition (1995), describes compositions and formulations suitable for pharmaceutical delivery of the compounds disclosed herein.

Compositions comprising one or more of the disclosed compounds typically comprise from greater than 0 up to 99% of the disclosed compound, or compounds, and/or other therapeutic agent by total weight percent. More typically, compositions comprising one or more of the disclosed compounds comprise from about 1 to about 20 total weight percent of the disclosed compound(s) and other therapeutic agent, and from about 80 to about 99 weight percent of a pharmaceutically acceptable excipient.

Preferably, the disclosed compound, combinations of disclosed compounds, or compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

In general, the nature of the excipient, such as a carrier, will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids.

The pharmaceutical compositions can be administered to subjects by a variety of mucosal administration modes, including by oral, rectal, ocular, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the disclosed compound(s) can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of 0.3 to 3.0, such as 0.5 to 2.0, or 0.8 to 1.7.

The disclosed compound(s), or a composition thereof, can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The disclosed compound(s), or a composition thereof, can be combined with the base or vehicle according to a variety of methods, and release of the compound can be by diffusion, disintegration of the vehicle, or associated formation of water channels. In some circumstances, the disclosed compound(s) or a composition thereof is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the disclosed compound(s), or a composition thereof, can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed compound can be brought about by including in the composition an agent which delays absorption, for example, monostearate salts and gelatin.

In certain embodiments, the disclosed compound(s) or a composition thereof can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the disclosed compound(s) and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(ε-caprolactone), poly(ε-caprolactone-CO-lactic acid), poly(ε-caprolactone-CO-glycolic acid), poly((β-hydroxy butyric acid), poly(alkyl-2-cyanoacrilate), hydrogels, such as poly (hydroxyethyl methacrylate), polyamides, poly(amino acids) (for example, L-leucine, glutamic acid, L-aspartic acid and the like), poly(ester urea), poly(2-hydroxyethyl-DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the disclosed compound(s) or a composition thereof can be delivered to a subject in a manner consistent with conventional methodologies associated with management of the disorder for which treatment or prevention is sought. In accordance with the disclosure herein, a prophylactically or therapeutically effective amount of the disclosed compound(s), or a composition thereof, is administered to a subject in need of such treatment for a time and under conditions sufficient to inhibit, and/or ameliorate a selected disease or condition or one or more symptom(s) thereof.

II. Administration

For prophylactic and therapeutic purposes, the disclosed compound(s), or a composition thereof, can be administered to the subject by an oral or ocular route or in a single bolus delivery, via continuous delivery (for example, continuous transdermal, mucosal, or intravenous delivery) over an extended time period, or in a repeated administration protocol (for example, by an hourly, daily or weekly, repeated administration protocol). The therapeutically effective dosage of the disclosed compound(s) can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the disclosed compound(s).

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. For guidance, the reader is referred to Fingl & Woodbury, "General Principles," In: *Goodman and Gilman's The Pharmaceutical Basis of Therapeutics*, latest edition, Pergamon Press, and the references cited therein. Initial dosages can also be estimated from in vivo data, such as animal models. Animal models useful for testing the efficacy of compounds to treat or prevent the various diseases described above are well-known in the art. Persons of ordinary skill in the art can adapt such information to determine dosages suitable for human and/or other animal administration.

The actual dosage will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum therapeutic response. A therapeutically effective amount is also one in which any toxic or detrimental side effects of the compound and/or other biologically active agent is outweighed in clinical terms by therapeutically beneficial effects.

Dosage amounts of the disclosed compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 10 mg/kg or to about 20 mg/kg per day, such as from 0.5 mg/kg to about 10 mg/kg per day or from about 0.7 mg/kg per day to about 5 mg/kg/day. Dosage amounts can be higher or lower depending upon, among other factors, the activity of the disclosed compound, its bioavailability, the mode of administration, and various factors discussed above.

Dosage can be varied by the attending clinician to maintain a desired concentration at a target site (for example, the lungs or systemic circulation). Higher or lower concentrations can be selected based on the mode of delivery, for example, trans-epidermal, rectal, oral, ocular, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

V. Examples

Example 1

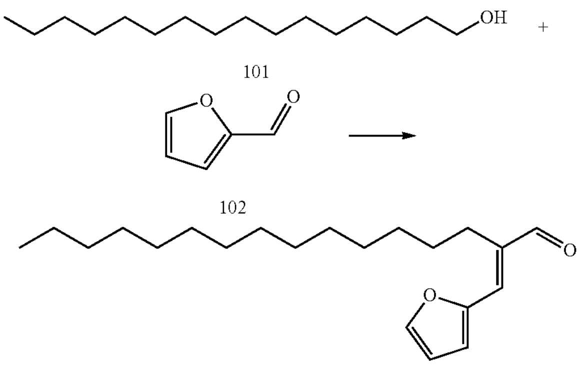

101

102

103

1 mmol of hexadecanol 101, a fatty alcohol, was combined with 2 mmol of furfural 102 in toluene solvent (1.5 mL) and mixed with 200 mg HT in a batch reactor. The mixture was heated at 150° C. under autogenous pressure for 20 hours resulting in compound 103 in a 75% yield.

Example 2

1 mmol of hexadecanol 101, 3 mmol of furfural 102, 1 mmol of triethylamine, and 0.05 mmol of nickel (II) acetylacetonate were mixed in a batch reactor. The mixture was heated at 180° C. under autogenous pressure for 20 hours. The reaction resulted in 90% yield of adduct 103.

Example 3

Four batch reactors were charged with 1 mmol of hexadecanol 101, 2 mmol of furfural 102 in cyclohexane solvent (1.5 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 40 mg $RuO_2 \cdot H_2O$. The mixture was heated at 180° C. under autogenous pressure for 22 hours. The reaction yielded 98% of compound 103, followed by 25% yield of products 104-107, with compounds 104 and 105 being the major products.

104

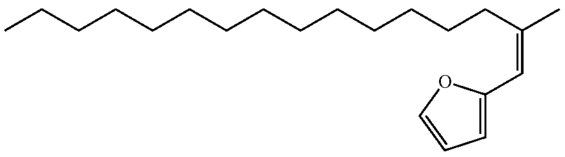

105

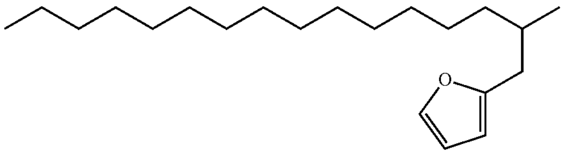

106

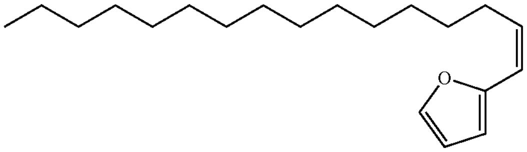

107

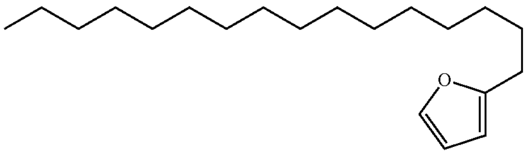

108

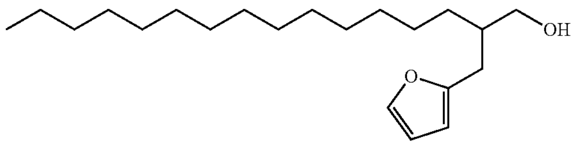

Example 4

Four batch reactors were charged with 1 mmol of hexadecanol 101, 2 mmol of furfural 102 in cyclohexane solvent (1.5 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 20 mg of $Pd/SiO_2$ and 40 mg $RuO_2 \cdot H_2O$. The mixture was heated at 180° C. under autogenous pressure for 22 hours. The reaction yielded 75% of compound 103, followed by 15% yield of products 104-107, with compounds 106 and 107 being the major products.

Example 5

Four batch reactors were charged with 1 mmol of hexadecanol 101, 2 mmol of furfural 102 in cyclohexane solvent (1.25 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 40 mg $RuO_2 \cdot H_2O$. The mixture was heated at 200° C. under autogenous pressure for 6 hours. The reaction yielded 79% of compound 103, followed by 97.8% yield of products 104-107, with compounds 104 and 105 being the major products.

Example 6

Four batch reactors were charged with 1 mmol of hexadecanol 101, 2 mmol of furfural 102 in cyclohexane solvent (1.25 mL) and 200 mg HT catalyst. The reactors were heated at 150° C. under autogenous pressure for 20 hours. The solids were separated from the reaction mixtures and the resulting liquids were combined. 0.5 mL of the combined liquid was mixed with 2.5 mL of 2-pentanol, 40 mg of Ru/C and 200 mg $In_2O_3$. The mixture was heated at 200° C. under autogenous pressure for 20 hours. The reaction yielded 76% of compound 103, followed by 49.4% yield of products 104-108, with compounds 104, 105 (17.9% sum) and 108 (25.7% sum) being the major products.

Example 7

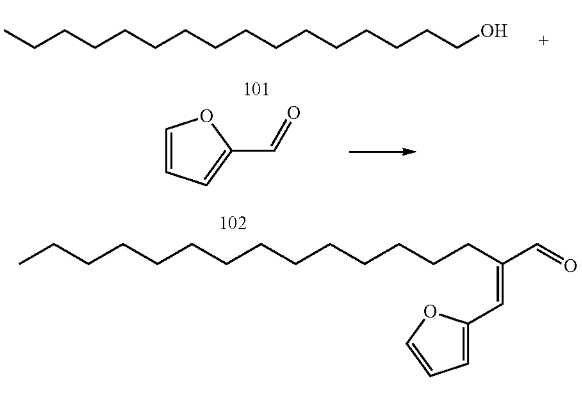

101

102

103

-continued

103

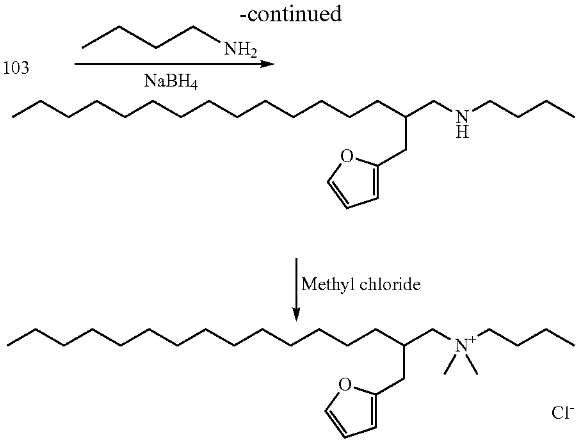

Seven batch reactors were charged with 1 mmol of 1-octanol 101, 2 mmol of furfural 102 in cyclohexane solvent (1.25 mL) and 400 mg HT catalyst. The reactors were heated at 150° C. under autogenous pressure for 20 hours. The solids were separated from the reaction mixtures and the resulting liquids were combined. The solids were washed with 25 mL of ethanol. The mixture of ethanol, cyclohexane and compound 103 was then mixed with 40 equivalents of n-butylamine (28 mL). The mixture was stirred for 1 hour. Then, 10 equivalents of NaBH 4 were added (265 mg) and the mixture was stirred for 24 hours. Then, 50 mL water were added to the mixture, which was stirred for 1 hour. The product was extracted with 50 mL of cyclohexane. An 1 mL aliquot of the cyclohexane extract was then pressurized to 4 atm with methyl chloride and heated to 70° C. for 24 hours. Compound 54 was extracted with deuterium oxide.

Example 8

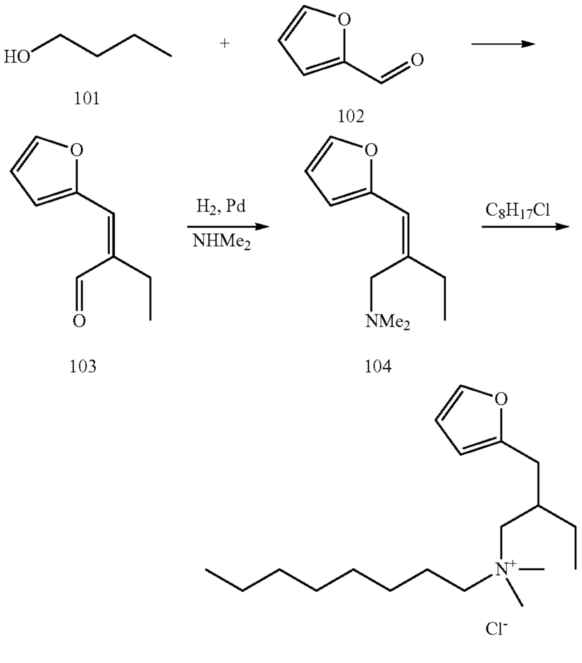

In a liquid phase batch reactor system, 2 g of furfural 102 and 0.74 g of 1-butanol 101 (mole ratio of furfural to 1-butanol was 2:1) were added along with 12.5 mL of cyclohexane and 2 g of HT catalyst. The reactors were heated at 150° C. under autogenous pressure for 20 hours. The product 103 was isolated by evaporation of the solvents under reduced pressure.

1.88 g of Product 103 were mixed with 8.2 g of dimethylamine (11% in isopropanol), 10 mL of isopropanol solvent and 0.5 g of 4% Pd/$SiO_2$ catalyst (4% weight) then set into the Parr multiple reactor system. The reactor was pressurized to 15 bar $H_2$ and heated to 130° C. for 2 hours. The resulting product 104 was mixed with 4.46 g of 1-chlorooctane (1:5 in mole ratio) and 20 mL of acetone solvent. It was then heated to 70 for 24 hours. Product 105 was isolated by evaporation of the solvents under reduced pressure.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula

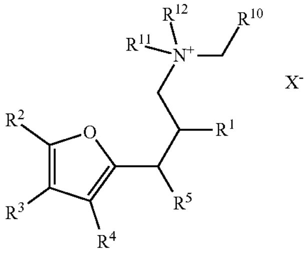

wherein:

$R^1$ is optionally substituted $C_{6-20}$alkyl;

each of $R^2$, $R^3$, and $R^4$ independently is H, $C_{1-6}$alkyl, aldehyde, or OH;

$R^5$ is H or $C_{1-3}$alkyl;

$R^{10}$ is optionally substituted $C_{2-20}$aliphatic;

each of $R^{11}$ and $R^{12}$ independently is H or $C_{1-6}$alkyl; and

X is halide or OH.

2. The compound of claim 1 wherein $R^1$, $R^{10}$ or both are independently substituted with one or more hydroxy, amine, or carbonyl moieties, or a combination thereof.

3. The compound of claim 1, wherein $R^1$ is $C_{6-18}$alkyl.

4. The compound of claim 1, wherein $R^{10}$ is $C_{2-4}$alkyl.

5. The compound of claim 1, wherein each of $R^{11}$ and $R^{12}$ independently is $C_{1-6}$alkyl.

6. The compound of claim 1, wherein one or both of $R^{11}$ and $R^{12}$ is methyl.

7. The compound of claim 1, wherein each of $R^2$, $R^3$, and $R^4$ independently is H or $C_{1-6}$alkyl.

8. The compound of claim 1, wherein $R^2$, $R^3$, and $R^4$ are all H.

9. The compound of claim 1, wherein X is Cl, Br, I or OH.

10. The compound of claim 1, wherein:

$R^1$ is $C_6$alkyl;

$R^{10}$ is $C_3$alkyl;

$R^2$, $R^3$, and $R^4$ are all H;

$R^{11}$ and $R^{12}$ are both methyl; and

X is Cl.

11. A pharmaceutical composition comprising a compound according to claim 1, and a pharmaceutically acceptable excipient.

12. A method of making a compound according to claim 1, the method comprising:

a) forming a mixture comprising a compound having a formula A-1

A-1

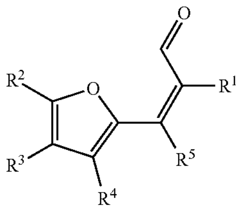

and a compound having a formula

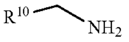

to form a compound having a formula A-2

A-2

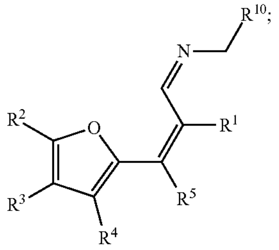

b) exposing the compound having formula A-2 to reducing conditions to form a compound having a formula A-3

A-3

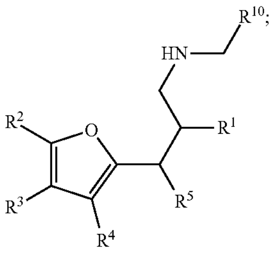

and c) treating the compound having the formula A-3 with a compound of formula $R^{11}X$ and a compound of formula $R^{12}X$ to form a compound having a formula A-4

A-4

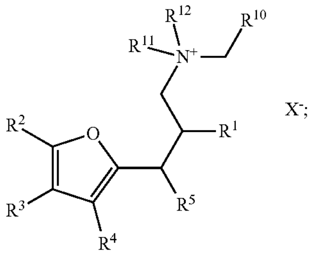

wherein $R^1$ is optionally substituted $C_{6-20}$alkyl;

each of $R^2$, $R^3$, and $R^4$ independently is H, $C_{1-6}$alkyl, aldehyde, or OH;

$R^5$ is H or $C_{1-3}$alkyl;

$R^{10}$ is optionally substituted $C_{2-20}$aliphatic;

each of $R^{11}$ and $R^{12}$ independently is H, or $C_{1-6}$alkyl; and each X independently is halide or OH.

13. The method of claim 12 wherein exposing the compound having formula A-2 to reducing conditions comprises treating the compound with a reducing agent or hydrogen gas in the presence of a catalyst.

14. The method of claim 13, wherein:

the reducing agent is a borohydride reagent; or the catalyst is a palladium-based catalyst.

15. The method of claim 12, wherein each X is Cl or Br.

16. A method of making a compound according to claim 1, the method comprising:

a) forming a mixture comprising a compound having a formula A-1

A-1

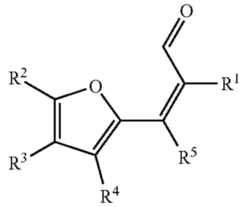

and a compound having a formula

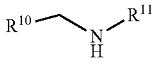

and exposing the mixture to reducing conditions to form a compound having a formula A-5

A-5

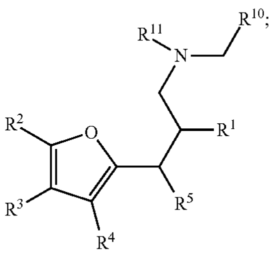

and and b) treating the compound having the formula A-5 with a compound of formula $R^{12}X$ to form a compound having a formula A-6

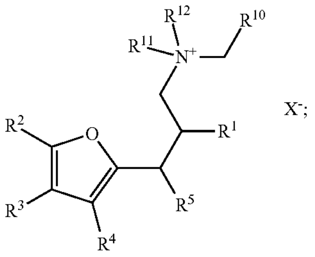

A-6 wherein $R^1$ is optionally substituted $C_{6-20}$alkyl;

each of $R^2$, $R^3$, and $R^4$ independently is H, $C_{1-6}$alkyl, aldehyde, or OH;

$R^5$ is H or $C_{1-3}$alkyl;

$R^{10}$ is optionally substituted $C_{2-20}$aliphatic;

each of $R^{11}$ and $R^{12}$ independently is H, or $C_{1-6}$alkyl; and each X independently is halide or OH.

17. The method of claim 16 wherein exposing the mixture to reducing conditions comprises treating the compound with a reducing agent or hydrogen gas optionally in the presence of a catalyst.

18. The method of claim 17, wherein:

the reducing agent is a borohydride reagent; or the catalyst is a palladium-based catalyst.

19. The method of claim 16, wherein each X is Cl or Br.

* * * * *